United States Patent [19]
Prince

[11] Patent Number: 5,086,378
[45] Date of Patent: Feb. 4, 1992

[54] FIBER OPTIC FINGER LIGHT

[76] Inventor: Mark W. Prince, 906 S. Farmerville, Ruston, La. 71270

[21] Appl. No.: 569,715

[22] Filed: Aug. 20, 1990

[51] Int. Cl.$^5$ .................. F21L 15/12; F21V 8/00
[52] U.S. Cl. ..................... 362/103; 362/32; 362/251; 362/800
[58] Field of Search ............ 362/103, 104, 109, 32, 362/800, 198, 184, 200, 231, 234, 249, 251, 394, 396, 191; 350/96.1, 96.15, 96.18

[56] References Cited

U.S. PATENT DOCUMENTS

| | | | |
|---|---|---|---|
| 674,770 | 5/1901 | Hull | 362/103 |
| 914,975 | 3/1909 | Radley | 362/103 |
| 918,181 | 4/1909 | Meadows | 362/103 |
| 1,245,817 | 11/1917 | Suserud | 362/103 |
| 1,553,860 | 9/1925 | Hopper | 362/103 |
| 1,754,570 | 4/1930 | Pickett | 362/104 |
| 3,112,889 | 12/1963 | Marmo et al. | 362/103 |
| 4,302,797 | 11/1981 | Cooper | 362/32 |

FOREIGN PATENT DOCUMENTS

| | | | |
|---|---|---|---|
| 51401 | 3/1936 | Denmark | 362/103 |
| 455972 | 7/1891 | France | 362/103 |
| 1514969 | 1/1968 | France | 362/109 |
| 409403 | 5/1934 | United Kingdom | 362/103 |
| 1186602 | 4/1970 | United Kingdom | 362/109 |

Primary Examiner—Ira S. Lazarus
Assistant Examiner—Y. Quach
Attorney, Agent, or Firm—John M. Harrison

[57] ABSTRACT

A fiber optic finger light for use by pilots, navigators and aircraft crew during night flying, which fiber optic finger light includes, in a most preferred embodiment, green and red light-omitting diodes (LED) mounted in a housing adapted for strapping to one hand and operated by a 3-position switch. A lens is mounted forwardly of each of the light-emitting diodes and serves to selectively focus light from the light-emitting diodes on one end of one of a pair of light-transmitting fibers which extend through the housing and project from the housing in a flexible duplex fiber optic cable. The light housing is strapped to the wrist and the fiber optic duplex cable is strapped to a finger, such that red or green light emitted from the LED at the opposite end of the optic fiber by manipulation of the switch, may be focused on charts, instruments check lists and the like, in the aircraft.

20 Claims, 2 Drawing Sheets

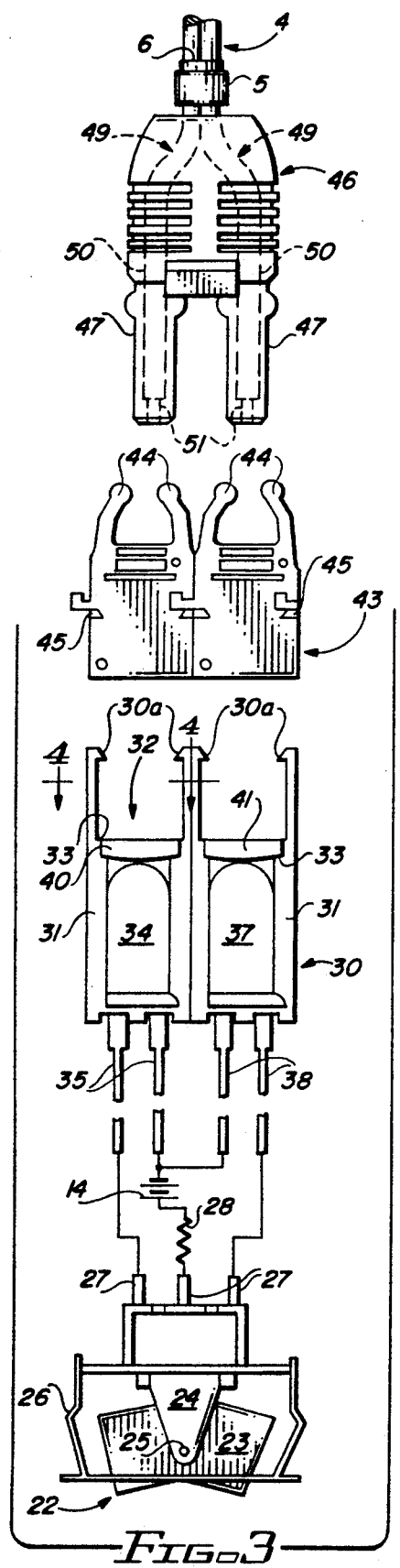
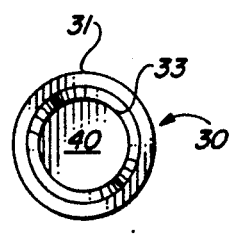
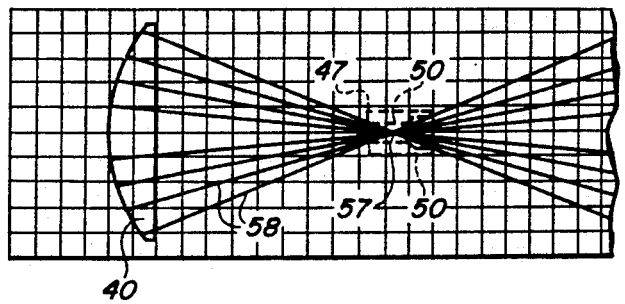
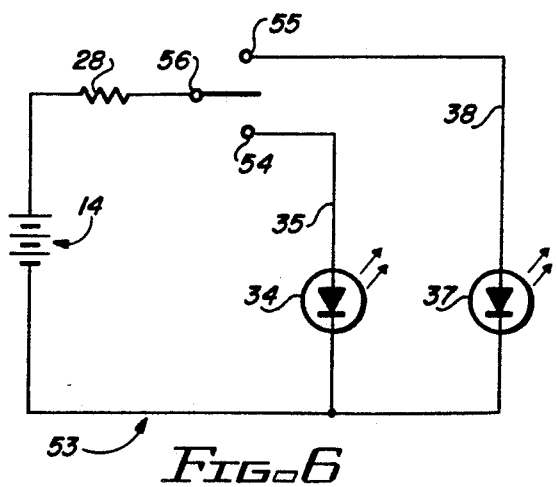

FIBER OPTIC FINGER LIGHT

BACKGROUND OF THE INVENTION

FIELD OF THE INVENTION

This invention relates to apparatus for improving visual resolution in the cockpit of an aircraft at night and more particularly, to a fiber optic finger light which includes at least one light-emitting diode capable of emitting light of selected color, and most preferably, green and red light-emitting diodes (LED) mounted in a housing adapted for strapping to one hand and operated by a 3-position switch. A lens is mounted forwardly of each of the light-emitting diodes and focuses light from a selected one of the light-emitting diodes on one end of one of a pair of light-transmitting fibers, which fibers extend through the housing in a pair of fiber optic simplex cables which join at a flexible duplex fiber optic cable mounted on the housing. When the duplex fiber optic cable is strapped to a finger and the housing strapped to the wrist, red or green light is selectively emitted from the opposite end of the corresponding optic fiber by manipulation of the switch for focussing on charts, instruments, check lists and the like, in the aircraft.

On today's modern battlefield, many wars are being fought at night. The United States military has been preparing for such night action by using night vision devices such as second generation PVS-5 and third generation ANVIS-6 night vision goggles. Imaging systems have been used extensively in Marine Aviation since 1986 and since that time, the introduction of the ANVIS-6 night vision goggles has greatly enhanced the capability and survivability of both crews and aircraft. The military is moving toward complete integration of ANVIS equipment over the older PVS system, since the former represents the current state of the art in night vision imaging. Development of the ANVIS-6 has doubled the goggle reliability to a system life span of over 7500 hours. In addition to this significant life span extension, the system was designed from the outset for aviators, rather than slow moving ground vehicles, for which the earlier PVS-5 system was developed. The third generation goggles facilitate in-flight adjustment by means of knobs that move the goggles fore and aft, up and down and allow eye span and focal adjustment. These improvements allow the pilot the option and accessibility to make fine adjustments in flight, which option was not available in the older PVS-5 system.

Night vision goggles facilitate significant enhancement of visual references over the unaided eye. However, among the several problems associated with these night vision goggle apparatus are:

1. A limited field of view from the normal horizontal field of view of 200 degrees to only 40 degrees, when all the proper adjustments are made to the equipment.

2. The goggles allow the user to see the size of visualized objects but does not facilitate depth perception.

3. There is a difference in visual acuity or the ability to resolve detail. All Naval Aviators are required to possess 20/20 visual acuity unless a waiver is obtained to enter flight school. In order to conduct Carrier Qualifications (shipboard landings) the minimum visual acuity a pilot may possess is 20/50, corrected to 20/20 with the use of glasses. However, shipboard operations are continuously being conducted by pilots flying on PVS-5 systems at 20/50 (optimum conditions) and 20/40 on the ANVIS-6 apparatus. When operated under starlight conditions, the visual acuity drops to 20/80 on ANVIS-6 and 20/100 while using PVS-5's.

Supplemental cockpit lighting is extremely important in night flying, since the pilot must integrate visual cues supplied by the goggles and combine this with information gained by the flight instruments. This is very critical in many aerial operations, for example, while flying close to the ground in helicopters during missions.

Marine aircraft are equipped with a "quick fix" interim, which consists of a blue light kit that can be quickly installed while the aircraft is on the ground. The kit contains various sized lenses to fit over peanut lights, map lights, secondary console lights and other light emitting sources. These blue lenses filter out the light which degrade the capability of the goggles.

Red, white and yellow light shut down the Anvis-6 system. Red is the color of standard night instrumentation lighting and a filter to shut out wave lengths in the blue-green spectrum has been installed in the ANVIS-6 system and this expedient facilitates the use of blue lenses.

Although not located on the individual instruments, secondary lighting is located in the cockpit of an aircraft to illuminate the primary flight and engine instruments. A primary problem associated with the location of secondary lights lies in the fact that the intensity required to illuminate the instruments located farthest from the light source causes windshield glare and, in turn, degradated performance of the goggles, especially during low ambient light, such as starlight.

The cost involved in changing the individual instrument lighting system in aircraft is enormous, and two alternatives are possible:

1. Remove all light-emitting bulbs in the aircraft cockpit and replace them with blue-green bulbs that have either a blue or green coating or tinted glass that operate within the parameters of the night vision devices; or 2. Incorporate an auxiliary light that is compact, portable and reliable and can be used in the goggle environment and on regular night missions. I therefore describe herein a light-weight, reliable finger light that incorporates a blue or green light with a red light, using fiber optics.

DESCRIPTION OF THE PRIOR ART

Various types of portable and hand-held lights are known in the art. An early "Electric Lamp" is detailed in U.S. Pat. No. 674,770, dated May 21, 1901, to C. B. Hull. The electric lamp includes a cylindrical housing fitted with a reflector and an incandescent bulb, with finger rings attached to the housing for handling purposes. U.S. Pat. No. 914,975 dated Mar. 9, 1909, to G. R. Radley, details a "Portable Electric Light" which is similar in design, having a ring fitting for mounting on a thumb and used to read a book in the dark. An "Electric Flash Light Attachment" is detailed in U.S. Pat. No. 918,181, dated Apr. 13, 1909, to F. Meadows. The apparatus is likewise provided with a finger ring for securing a small, portable light on the finger of one hand. U.S. Pat. No. 1,245,817, dated Nov. 6, 1917, to H. Suserud, details a "Flash Light Carrier" which includes a wrist strap for carrying a battery and a flexible cord attached to the battery and fitted with a light bulb at one end. A finger clip is attached to the cord for attaching the cord to the thumb of the hand and illuminate a writing surface. U.S. Pat. No. 1,754,570, dated Apr. 15, 1930, to J. P. Pickett, details a Flash Light Having a Battery, a flexible cord attached to the battery, a light bulb attached to the end of the cord and a finger ring for fitting the light bulb on the finger and illuminating a work area. U.S. Pat. No. 3,112,889, dated Dec. 3, 1963, to M. L. Marmo, et al, details a "Wrist Supported Flashlight". The flashlight is attached to a wrist strap for mounting on top of the hand and illuminating a work area. The Marine Corps uses a finger-mounted, green light-emitting diode light for illuminating various instruments during night flying.

It is an object of this invention to provide a portable fiber optic finger light which is easily strapped to the finger and wrist of a user and utilized to illuminate instruments, check lists and the like in an aircraft.

Another object of this invention is to provide a fiber optic finger light which is characterized by a housing fitted with a wrist strap for mounting on the wrist of the user, at least one light-emitting diode of selected color mounted in the housing, with a lens provided in alignment with each of the light-emitting diodes for focusing light from the light-emitting diode(s) onto one or more light-emitting fibers extending from the housing through a flexible duplex fiber optic cable and a switch connected to a battery and the light-emitting diode(s), for selectively energizing one of the light-emitting diodes and focusing the light on the corresponding fiber to emit the light from the end of the duplex fiber optic cable.

Yet another object of this invention is to provide a fiber optic finger light which is characterized by a pair of light-emitting diodes (LED) and lenses mounted in a housing in cooperation with a pair of light-transmitting fibers which extend from the housing through a duplex fiber optic cable and a switch for selectively energizing a selected LED, along with a wrist strap and finger strap attached to the housing and the duplex fiber optic cable, respectively, for focusing light of a selected color on the instruments in an aircraft.

Still another object of the invention is to provide a new and improved, battery-operated fiber optic finger light for strapping to the hand and finger and illuminating instruments and the like in aircraft, which fiber optic finger light includes a 3-position switch electrically connected to the battery and a pair of light-emitting diodes seated in an LED housing, a pair of lenses provided in the LED housing forwardly of the light-emitting diodes, a horizontal module removably attached to the LED housing, a duplex connector removably attached to the horizontal module and a flexible duplex fiber optical cable extending from the duplex connector for transmitting light from the light-emitting diodes in sequence by operation of the switch.

SUMMARY OF THE INVENTION

These and other objects of the invention are provided in a new and improved fiber optic finger light which is light in weight, portable and includes a housing containing a battery, a three-position switch, a pair of light-emitting diodes (LED) of selected color wired to the switch and battery and a pair of lenses provided in cooperation with the LED for focusing light on the ends of a pair of light-transmitting cables which extend through the housing in a pair of simplex fiber optic cables that join to define a flexible duplex fiber optic cable extending from the housing, wherein the housing and duplex fiber optic cable can be strapped to the wrist and fingers, respectively, of a user and the light from a light-emitting diode energized by operation of the switch and utilized to illuminate instruments, check lists and the like in the cockpit and elsewhere in an aircraft.

BRIEF DESCRIPTION OF THE DRAWINGS

The invention will be better understood by reference to the accompanying drawings, wherein:

FIG. 3 is a fully exploded view of the components of the fiber optic finger light illustrated in FIGS. 1 and 2;

FIG. 4 is a sectional view taken along line 4—4 of the LED lense housing illustrated in FIG. 3;

FIG. 5 is a pictorial illustration of the operation of one of the LED lenses located inside the LED lense housing illustrated in FIG. 3; and FIG. 6 is a schematic of a preferred electrical circuit for selectively energizing the respective light-emitting diodes located in the LED lense housing illustrated in FIG. 3.

DESCRIPTION OF THE PREFERRED EMBODIMENTS

Figure 1:
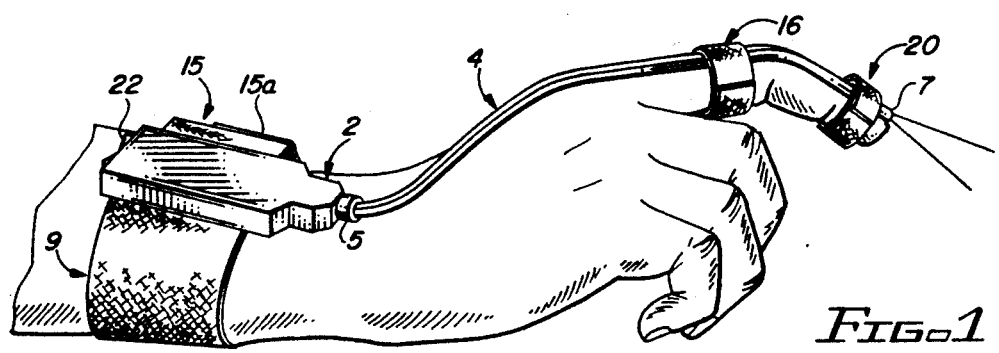
FIG. 1 is a perspective view of a preferred embodiment of the fiber optic finger light of this invention attached to the wrist of a user.
Figure 2A:
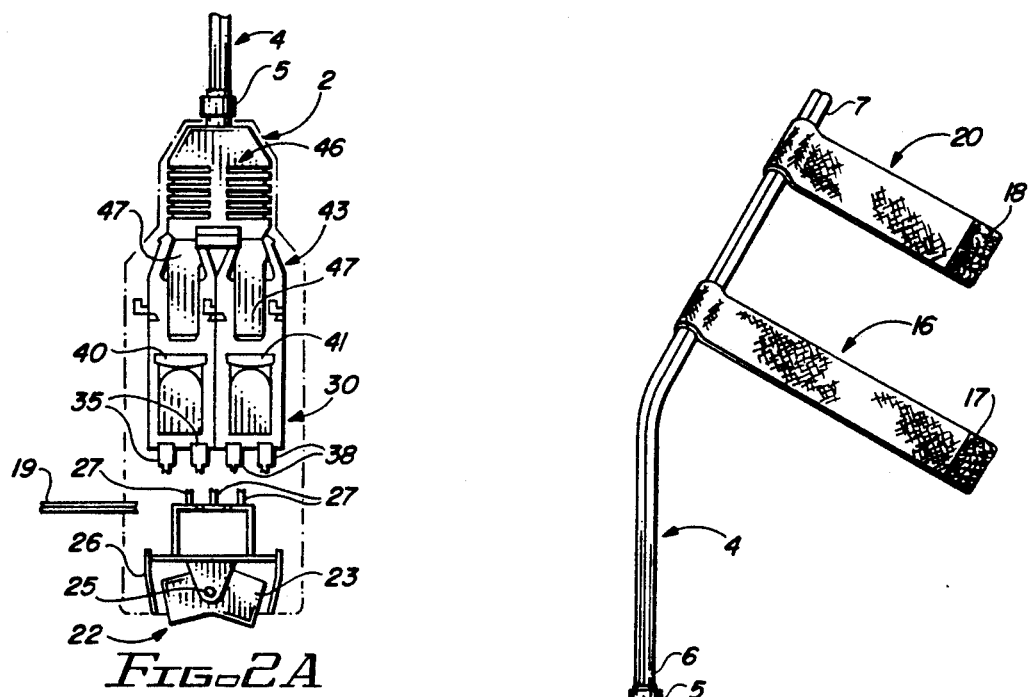
FIG. 2 and 2a is a partially exploded view of the fiber optic finger light illustrated in FIG. 1.
Figure 2:
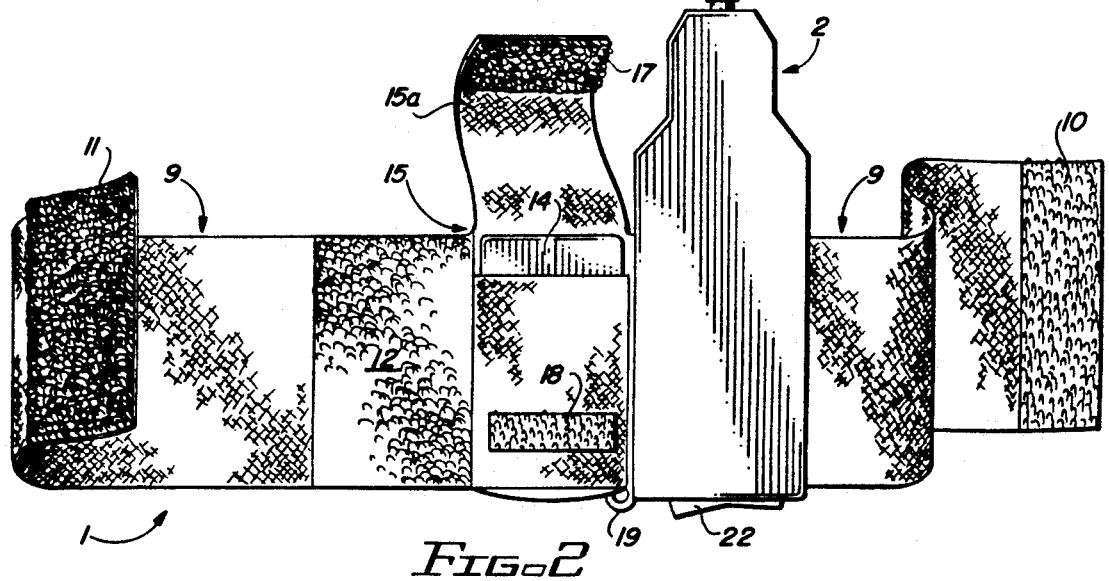

Referring initially to FIGS. 1 and 2 of the drawings, the fiber optic finger light of this invention is generally illustrated by reference numeral 1. The fiber optic finger light 1 is characterized by a light housing 2, fitted with a housing pile strip (not illustrated) for selectively engaging one of two housing loop strips 12 located on the wrist strap 9, as illustrated in FIG. 2, and removably securing the light housing 2 on the wrist of a user. An elongated, flexible duplex fiber optic cable 4 projects from one end of the light housing 2 at a ring fitting 5, which crimps the housing end 6 of the duplex fiber optic cable 4 to the light housing 2. An outside finger strap 20 is secured to the light-emitting end 7 of the duplex fiber optic cable 4, while an inside finger strap 16 is attached to the duplex fiber optic cable 4 between the outside finger strap 20 and the housing end 6 of the duplex fiber optic cable 4. Each of the inside finger straps 16 and outside finger straps 20 are fitted with a finger strap pile element 17 on one side thereof and a finger strap loop element 18 on the opposite side thereof, respectively, for securing the inside finger strap 16 and the outside finger strap the reference numeral 20 to the finger of one hand, as further illustrated in FIG. 1. Similarly, the wrist strap 9 is fitted with a wrist strap pile element 10 and a cooperating wrist strap loop element 11, for securing the wrist strap 9 on the wrist of the user.

Referring now to FIGS. 1-3 and 6 of the drawings and initially again to FIG. 2, a battery 14 is seated in a battery pouch 15 attached to the wrist strap 9 and removably secured in the battery pouch 15 by pouch flap 15a. The battery 14 is connected by means of a wiring harness 19 (FIG. 2) to selected ones of the green LED leads 35 and red LED leads 38, as illustrated in FIGS. 3 and 6. Furthermore, the "off" switch terminal 27 of the switch 22 is also attached to the battery 14, as further hereinafter described. The switch 22 is located in the lower end of the light housing 2 and is characterized by a rocker tab 23, pivotally mounted on a rocker bracket 24 by means of a pin 25, as further illustrated in FIG. 3. The switch 22 is fitted inside a switch housing 26 and further includes additional switch terminals 27 that are attached to the green LED leads 35 and red LED leads 38, respectively. A resistor 28 is provided in series between the battery 14 and the "off" switch terminal 27, also as illustrated in FIG. 3.

Referring now to FIGS. 2-4 of the drawings, in a most preferred embodiment of the invention the light housing 2 encloses the 3-position switch 22 at the bottom thereof, a light-emitting diode (LED) housing 30 is positioned immediately adjacent the switch 22, a horizontal module 43 is seated on the LED housing 30 and a duplex connector 46 is mounted on the horizontal module 43. Accordingly, referring again to FIG. 2, when assembled, the switch 22, LED housing 30, horizontal module 43 and duplex connector 46 are oriented in a compact, stacked relationship inside the light housing 2. The rocker tab 23 of the switch 22 is partially exposed through an opening (not illustrated) located in the bottom of the light housing 2, to facilitate operation of the switch 22, as further hereinafter described.

Referring again to FIGS. 2-4 and particularly to FIG. 3 of the drawings, the LED housing 30 is characterized by a pair of adjacent LED receptacles 31, each having a round LED bore 32, with a lens shoulder 33 shaped therein. A green light-emitting diode (LED) 34 is seated in the bottom portion of one of the LED receptacles 31 and a green LED lens 40 is seated on the corresponding lens shoulder 33 provided in that LED receptacle 31. Similarly, a red light-emitting diode (LED) 37 is located in the bottom of the opposite LED receptacle 31 and a red LED lens 41 is provided on the corresponding lens shoulder 33 in the second LED receptacle 31. The green LED leads 35 extend from the green LED 34 through the bottom of the LED housing 30, while the red LED leads 38 extend from the red LED 37 through the bottom of the LED housing 30, as further illustrated in FIG. 3. As heretofore described, the green LED leads 35 and red LED leads 38 are connected to the battery 14 and to the appropriate switch terminals 27 of the switch 22. The upper edges of the LED receptacles 31 are fitted with housing tabs 30a, for engaging corresponding tab receptacles 45, located in the horizontal module 43, which seats on the LED housing 30, as illustrated in FIG. 2. Two pairs of spaced leg receptacles 44 are provided in the top of the horizontal modules 43 for receiving the parallel, hollow connector legs 47, extending from the duplex connector 46. Accordingly, the connector legs 47 fit inside the respective leg receptacles 44 of the horizontal module 43 when the fiber optic finger light 1 is assembled as illustrated in FIG. 2. The duplex fiber optic cable 4 extending from the top of the duplex connector 46 is split into a pair of simplex cables 49 inside the duplex connector 46, each of which simplex cables 49 is illustrated in phantom and extends through a separate connector leg 47. Each simplex cable 49 is characterized by simplex cable insulation 50, which protects a concentrically-located light transmitting fiber 51, the end of each of which light-transmitting fibers 51 is exposed at the extending ends of the connector legs 47, respectively, as further illustrated in FIG. 3.

Referring now to FIGS. 3 and 6 of the drawings, the electric circuit 53 is designed to facilitate operation of either the green LED 34 or the red LED 37 by operation of the switch 22. For example, manipulation of the rocker tab 23 element of the switch 22 such that rocker tab 23 engages the green LED switch contact 54, illustrated in FIG. 6, energizes the green LED 34. Conversely, operation of the rocker tab 23 to engage the red LED switch 55, energizes the red LED 37. Manipulation of the rocker tab 23 to engage the "off" switch contact 56 neutralizes the system and maintains both the green LED 34 and the red LED 37 in the "off" position. In a most preferred embodiment of the invention, the battery 14 shown in the electric circuit illustrated in FIG. 6 is characterized by a 9-volt alkaline battery, while the resistor 28 is a 100 ohm, ½ watt resistor.

Referring now to FIGS. 2 and 5 of the drawing, the fiber optic finger light 1 is assembled as illustrated in FIG. 2, such that the distances between the green LED lens 40 and the corresponding extending end of the corresponding one of the connector legs 47, and between the red LED lens 41 and the other connector leg 47, are such that the focal point 57 of the light rays 58 transmitted from the green LED 34 and the red LED 37, respectively, is located just inside each of the connector legs 47. Referring to FIG. 5, this light wave convergence or focal point 57 is located at or very close to the extending end of the light transmitting fibers 51, respectively, in order to transmit light from this end of the light-transmitting fibers 51, respectively, to the opposite end of the light transmitting fibers 51, which terminate at the light-emitting end 7 of the duplex fiber optic cable 4.

Accordingly, referring again to FIGS. 1 and 2 of the drawings, when it is desired to use the fiber optic finger light 1, the light housing 2 is positioned on either of the two housing loop strips 12 located on either side of the battery pouch 15, depending upon whether the user is right-handed or left-handed and is secured in place by matching the housing pile strip (not illustrated) with the selected housing loop strip 12. When this selection is made, the wrist strap 9 is wrapped around the wrist and is secured by connecting the wrist strap pile element 10 to the wrist strap loop element 11. The duplex fiber optic cable 4 is then extended along one of the fingers and the inside finger strap 16 and outside finger strap 20 are wrapped around the finger in spaced relationship and secured by means of the cooperating finger strap pile elements 17 and finger strap loop elements 18, respectively. The light-emitting end 7 of the duplex fiber optic cable 4 can then be manipulated and aimed at a specific instrument check list or the like, by moving the finger and the switch 22 operated to project either red or green light from the light-emitting end 7 of the duplex fiber optic cable 4. The fiber optic finger light 1 is therefore quickly and easily, yet removably, attached to the wrist and finger of either hand, leaving the other hand free for operating the aircraft or other tasks.

It will be appreciated by those skilled in the art that light-emitting diodes of various colors other than red and green can be utilized in the fiber optic finger light of this invention, as desired. Accordingly, if the green LED 34 and/or red LED 37 must be exchanged for LED's of different color, the horizontal module 43 and attached duplex connector 46 can be removed from the adjacent LED housing 30 by releasing the respective housing tabs 30a from corresponding tab receptacles 45, the green LED lens 40 and/or red LED lens 41 removed from the respective lens shoulders 33 and the green LED 34 and/or red LED 37 then removed from the interior of the respective LED receptacle 31. Replacement light-emitting diodes can be easily installed by reversing this procedure and reassembling the horizontal module 43 on the LED housing 30, as described above.

It will be further appreciated by those skilled in the art that under circumstances where the duplex connector 46, horizontal module 43 and LED housing 30 are utilized in the light housing 2 as described above, the duplex fiber optic cable 4 may be characterized by a Hewlett Packard Duplex Fiber Optic Cable #HFBR-PMD, the duplex connector 46 may be a Hewlett Packard Duplex Connector HFBR-4506 and the horizontal module 43 may be characterized by a Hewlett Packard Horizontal Module HFBR-1521/1522/1523/1524. The LED housing 30 is custom-designed to receive the respective green LED 34, red LED 37, green LED lens 40 and red LED lens 41, and to fit on the bottom of the horizontal module 43, as illustrated in FIGS. 2 and 3. As heretofore described, the switch 22 is characterized by a three-position switch (on-off-on), as detailed in FIGS. 3 and 6, when two LEDS are utilized in the fiber optic finger light 1.

It is understood that a single LED may be used in the LED housing 30, along with a single lens, if light of only color is desired. Under these circumstances, the switch 22 may be 2-position in design, with an on-off sequence. Furthermore, it will also be appreciated that more than two LED may be utilized if light beams of more than two colors are desired. The switch 22 must then be designed with sufficient contacts to selectively energize each such LED, as required.

It will be further understood that although the modular construction detailed above and illustrated in the drawings is a preferred construction for the fiber optic finger light of this invention, alternative constructions, including a two-piece injection-molded light housing 2, with interior cavities for receiving the various LED, lenses and even the battery 14, as well as the light-transmitting fibers 51, may also be used. Other options include separate molded compartments containing various numbers of LED and lenses, of either replacement or disposable design.

Another variation of the fiber optic finger light of this invention includes connecting the LED circuit and switch to an external power source located in the aircraft, instead of using the battery 14.

It will be understood and appreciated that the fiber optic finger light of this invention can be utilized with both the PVS-5 and ANVIS-6 night vision goggle systems, as well as other night vision goggle systems known to those skilled in the art. Furthermore, the fiber optic finger light has wide application, not only in aircraft of all designs, but also in any environment where low intensity supplemental lighting is needed for night activities and additional illumination is necessary to illuminate instruments, check lists, and the like.

Accordingly, while the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A fiber optic finger light for mounting on the wrist and finger of a user, comprising a housing; wrist strap means attached to said housing for removably securing said housing on the wrist; at least one light-emitting diode provided in said housing; at least one lens positioned in said housing in light-receiving relationship with respect to said light-emitting diode; fiber optic cable means extending from said housing for receiving and transmitting light from said light-emitting diode through said lens; finger attachment means carried by said fiber optic cable means for securing said fiber optic cable means to the finger; and switch means electrically connected to a source of electric current and said light-emitting diode, whereby said light-emitting diode is selectively energized to emit light through said lens and said fiber optic cable means responsive to manipulation of said switch means.

2. The fiber optic finger light of claim 1 wherein said at least one light-emitting diode further comprises a pair of light-emitting diodes, said at least one lens further comprises a pair of lenses aligned with said light-emitting diodes, respectively, and said switch means further comprises a three-position switch having an on-off-on sequence.

3. The fiber optic finger light of claim 1 wherein said finger attachment means further comprises a pair of finger straps attached to said fiber optic cable means.

4. The fiber optic finger light of claim 1 wherein:
(a) said at least one light-emitting diode further comprises a pair of light-emitting diodes, said at least one lens further comprises a pair of lenses aligned with said light-emitting diodes, respectively, and said switch means further comprises a three-position switch having an on-off-on sequence; and
(b) said finger attachment means further comprises a pair of finger straps attached to said fiber optic cable means in spaced relationship.

5. The fiber optic finger light of claim 1 further comprising an LED housing provided in said housing for containing said light-emitting diode and said lens and a horizontal module provided in said housing and adapted for attachment to said LED housing and wherein said switch means is located adjacent to said LED housing, said fiber optic cable means further comprises a duplex connector provided in said housing and adapted for attachment to said horizontal module, at least one simplex fiber optic cable provided in said duplex connector in spaced relationship with respect to said lens, respectively, and a flexible duplex fiber optic cable extending from said simplex fiber optic cable and said duplex connector and said housing and said finger attachment means is attached to said duplex fiber optic cable.

6. The fiber optic finger light of claim 5 wherein said at least one light-emitting diode further comprises a pair of light-emitting diodes, said at least one lens further comprises a pair of lenses aligned with said light-emitting diodes, respectively, and said switch means further comprises a three-position switch having an on-off-on sequence.

7. The fiber optic finger light of claim 5 wherein said finger attachment means further comprises a pair of finger straps attached to said duplex fiber optic cable in spaced relationship.

8. The fiber optic finger light of claim 5 wherein:
(a) said at least one light-emitting diode further comprises a pair of light-emitting diodes, said at least one lens further comprises a pair of lenses aligned with said light-emitting diodes, respectively, and said switch means further comprises a three-position switch having an on-off-on sequence; and
(b) said finger attachment means further comprises a pair of finger straps attached to said duplex fiber optic cable in spaced relationship.

9. The fiber optic finger light of claim 1 wherein said source of electric current is a battery and further comprising battery attachment means provided on said wrist strap means for securing said battery to said wrist strap means.

10. The fiber optic finger light of claim 1 wherein:
   (a) said at least one light-emitting diode further comprises a pair of light-emitting diodes, said at least one lens further comprises a pair of lenses aligned with said light-emitting diodes, respectively, and said switch means further comprises a three-position switch having an on-off-on sequence; and
   (b) said source of electric current is a battery and further comprising a battery pouch provided on said wrist strap means for securing said battery to said wrist strap means.

11. The fiber optic finger light of claim 10 wherein said finger attachment means further comprises a pair of finger straps attached to said fiber optic cable means.

12. The fiber optic finger light of claim 11 further comprising an LED housing provided in said housing for containing said light-emitting diodes and said lenses; a horizontal module provided in said housing and adapted for attachment to said LED housing; and wherein said three-position switch is located adjacent to said LED housing, said fiber optic cable means further comprises a duplex connector provided in said housing and adapted for attachment to said horizontal module, a pair of simplex fiber optic cables provided in said duplex connector in spaced relationship with respect to said lenses, respectively, and a flexible duplex fiber optic cable extending from said simplex fiber optic cables and said duplex connector and said housing and said finger straps are attached to said duplex fiber optic cable in spaced relationship.

13. A fiber optic finger light for mounting on the wrist and finger of a user, comprising a housing; wrist strap means attached to said housing for securing said housing on the wrist; a pair of light-emitting diodes provided in said housing, said light-emitting diodes each capable of emitting a light of different color; a pair of lenses positioned in said housing in light-receiving relationship with respect to said light-emitting diodes, respectively; fiber optic cable means extending from said housing for receiving and transmitting light from said light-emitting diodes through said lenses; finger strap means carried by said fiber optic cable means for securing said fiber optic cable means to the finger; and switch means electrically connected to a source of electric current and said light-emitting diodes, whereby said light-emitting diodes are selectively energized to emit light of corresponding color through one of said lenses and said fiber optic cable means responsive to manipulation of said switch means.

14. The fiber optic finger light of claim 13 wherein said switch means is mounted in said housing and further comprises a three-position switch having an on-off-on sequence.

15. The fiber optic finger light of claim 14 wherein said finger strap means further comprises a pair of finger straps attached to said fiber optic cable means in spaced relationship.

16. The fiber optic finger light of claim 15 wherein said source of electric current is a battery and further comprising battery attachment means provided on said battery for securing said battery to said wrist strap means.

17. A fiber optic finger light for mounting on the wrist and finger of a user, comprising a housing; a first element of a loop-pile fastener secured to said housing; a wrist strap having a second element of said loop-pile fastener for receiving said first element and removably securing said housing on said wrist strap; a pair of light-emitting diodes provided in said housing, said light-emitting diodes each capable of emitting a light of different color; a pair of lenses positioned in said housing in light-receiving relationship with respect to said light-emitting diodes, respectively; fiber optic cable means having one end located in spaced, light-focussed relationship with respect to said lenses, respectively, and the opposite end of said fiber optic cable means extending from said housing for receiving and transmitting light from said light-emitting diodes through said lenses; at least one finger strap means carried by said opposite end of said fiber optic cable means for securing said opposite end of said fiber optic cable means to the finger; a battery removably carried by said wrist strap; and switch means electrically connected to said battery and said light-emitting diodes, whereby said light-emitting diodes are selectively energized to emit light of corresponding color through one of said lenses and said fiber optic cable means responsive to manipulation of said switch means.

18. The fiber optic finger light of claim 17 wherein said switch means further comprises a three-position switch having an on-off-on sequence.

19. The fiber optic finger light of claim 17 wherein said at least one finger strap means further comprises a pair of finger straps attached to opposite end of said fiber optic cable means in spaced relationship.

20. The fiber optic finger light of claim 17 wherein:
   (a) said switch means further comprises a three-position switch having an on-off-on sequence; and
   (b) said at least one finger strap means further comprises a pair of finger straps attached to said opposite end of said fiber optic cable means in spaced relationship.

* * * * *